United States Patent [19]

Revici

[11] 4,301,150

[45] Nov. 17, 1981

[54] METHOD OF TREATING THE CLINICAL MANIFESTATIONS OF VIRAL DISEASES

[75] Inventor: Emanuel Revici, New York, N.Y.

[73] Assignee: The Vinoxen Company, Houston, Tex.

[21] Appl. No.: 102,487

[22] Filed: Dec. 11, 1979

Related U.S. Application Data

[63] Continuation of Ser. No. 852,946, Nov. 18, 1977, abandoned, which is a continuation of Ser. No. 597,179, Jul. 18, 1975, abandoned.

[51] Int. Cl.³ ...................... A61K 33/42; A61K 33/02
[52] U.S. Cl. ..................................... 424/128; 424/166
[58] Field of Search ................................ 424/128, 166

[56] References Cited

PUBLICATIONS

The Merck Index of Chemicals and Drugs, 6th Ed., (1952), p. 63.
The Dispensatory of the U.S.A., 24th Ed., 1947, p. 73.
Materia Medica and Therapeutics, 1907, pp. 236–239.
Sollman, A Manual of Pharmacology, 1957, p. 1050.

*Primary Examiner*—Jerome D. Goldberg
*Attorney, Agent, or Firm*—Millen & White

[57] ABSTRACT

The method of treating or alleviating the clinical manifestations of viral diseases which exhibit alkalosis which comprises administering to the host a non-toxic acidic salt of an inorganic acid.

12 Claims, No Drawings

METHOD OF TREATING THE CLINICAL MANIFESTATIONS OF VIRAL DISEASES

This is a continuation of application Ser. No. 852,946, filed Nov. 18, 1977, as a continuation of Ser. No. 597,179, filed July 18, 1975, both now abandoned.

SUMMARY OF THE INVENTION

A study of the clinical manifestations and analytical data of certain viral diseases, such as the common cold, have indicated that a dyschlorobiotic off-balance is present in the body. Local alkalosis of the nose and upper respiratory tract manifested by the rhinorrhea and tracheal and bronchial secretions exhibited by the common cold are apparently a consequence of this dyschlorobiosis. The secretions of the clinical manifestations of the common cold may have a pH as high as 8 to 8.5 depending on the severity of the cold.

This invention relates to an immediate means to combat these clinical manifestations of such viral diseases through the control of the alkalosis by administration to the body of acidifying compositions or compounds, such as non-toxic acidic salts of inorganic acids.

DESCRIPTION OF THE PREFERRED EMBODIMENTS

The non-toxic, water soluble acidic salts which can be used according to this invention include, without limitation, the ammonium salts of phosphoric acid, hydrochloric acid and sulfuric acid. Research to date has shown that mono-ammonium phosphate salt is considerably superior to other ammonium salts of inorganic acids. The mono-ammonium phosphate salt is also referred to as ammonium phosphate mono-basic. Ammonium phosphate hemi-basic is also included within the invention. The hemi-basic salt is strongly acid in reaction, while the mono-basic is mildly acid in reaction. Metal salts of the inorganic acids have not been found to be particularly effective, although some metal salts, particularly of an element of the first series of the Periodic Chart, such as lithium, potassium and cesium, could be used. Mixtures of the salts are also effective.

The inorganic acid ammonium salts of this invention are anti-pathogenic, and thus no claim is made that the acid ammonium salts act directly on or kill any virus or microorganism. Relief of the clinical manifestations or symptoms of the viral disease, however, relieves the body of a host defense function and thus aids the body's host defense system in attacking the virus in its normal manner, which may result in a faster cure than might normally be expected.

The amount of acidic inorganic salt administered is highly important. Little or no response is obtained when insufficient amounts are used. The exact amount to obtain relief of the symptoms of the viral disease will, of course, depend upon the particular symptoms and severity thereof exhibited by the person having the disease, the pH of the host, as well as the particular acidic inorganic salt being administered. Mildly acid salts will, of course, require higher dosages than strong acid salts. Research to date indicates that a sufficient amount of the acid salt should be administered to obtain a urine pH below about 5.5. With respect to mono-ammonium phosphate, one gram administered orally and repeated every half hour until the symptoms are fully controlled is recommended as a general rule, and for severe symptoms, higher doses, even up to 3 grams every half hour, may be used. Sufficient amounts of the acidic inorganic salts should be given to at least effect neutralization of the alkalosis of the host.

A study of the use of the ammonium salts has shown a low toxicity (acute, subacute, as well as chronic). No side effects were observed except that in a few cases, symptoms of gastric acidity were observed, especially when using high doses. By taking food together with the preparation, this occurrence is highly reduced. The mono-ammonium phosphate and the ammonium phosphate hemi-basic have a very low toxicity. Both have been used in the preparation of foods and mono-ammonium phosphate has been used for many years as a food additive. The estimated LD/50 of mono-ammonium phosphate in humans, based on tests in mice, is about 280 grams.

The inorganic acidic salts can be administered in any conventional manner such as by injection, but oral administration in gelatin capsules is the recommended manner of administration.

Approximately 100 patients having the common cold and exhibiting the normal symptoms therefrom, including rhinorrhea and tracheal and bronchial secretions and local alkalosis of the nose and upper respiratory tract, were treated by oral administration of 1 to 3 grams of mono-ammonium phosphate encased in a water soluble gelatinous capsule every half hour. The majority of the patients exhibited normal cold symptoms and were given 1 gram of mono-ammonium phosphate every half hour and the remainder who exhibited rather severe symptoms were given between 2 and 3 grams every half hour. Approximately 85 of the patients exhibited marked improvement with practically complete control of the cold symptoms within about 24 to 48 hours.

Fifteen patients having herpes simplex were treated with mono-ammonium phosphate administered orally at 1 gram every half hour. All patients responded showing distinct improvement with blisters disappearing within about 24 to 48 hours. Approximately 8 patients responded within the first day of treatment. Left by itself, the blisters normally persist for one week or more.

One patient with herpes zoster was treated with mono-ammonium phosphate administered orally at 1 gram every half hour. The patient responded within about 48 hours with substantial disappearance of the lesions. The pain, however, particularly at night, persisted. This is not unusual, however, since in the normal cure by the body host defense system, the pain occasionally persists after evidence of the inflammation has subsided.

Eighteen rabbits were inoculated with smallpox vaccine in the normal manner. The rabbits were divided into two groups of 9. The first group was given drinking water containing 2% by weight of mono-ammonium phosphate. The second group was given drinking water containing only 2% by weight salt. Both groups drank the normal amount of water. Within 24 hours the second control group developed strong very red inflammation in the inoculated area while the group to which mono-ammonium phosphate was given developed only tiny pink or brown spots.

I claim:

1. A method of treating or alleviating the clinical manifestations of viral diseases which exhibit local alkalosis, said manifestations including rhinorrhea, tracheal or bronchial secretions, which comprises internally administering to a patient having said viral disease a sufficient amount of a non-toxic, water soluble acidic ammonium salt of phosphoric acid or sulfuric acid to effectively neutralize the alkalosis and eliminate or alleviate said clinical manifestations.

2. The method of claim 1 in which the ammonium salt is mono-ammonium phosphate.

3. The method of claim 2 in which the ammonium salt is administered orally to the patient in an amount from about 1 gram to about 3 grams every half hour.

4. A method according to claim 1 wherein the patient exhibits clinical manifestations of herpes simplex disease.

5. The method of claim 4 in which the ammonium salt is mono-ammonium phosphate.

6. The method of claim 5 in which the ammonium salt is administered orally to the patient in an amount from about 1 gram to about 3 grams every half hour.

7. A method according to claim 1 wherein the patient exhibits the clinical manifestations of herpes zoster disease.

8. The method of claim 7 in which the ammonium salt is mono-ammonium phosphate.

9. The method of claim 8 in which the ammonium salt is administered orally to the patient in an amount from about 1 gram to about 3 grams every half hour.

10. A method according to claim 1 wherein the clinical manifestations are those resulting from the patient having been inoculated with smallpox vaccine.

11. The method of claim 10 in which the inorganic salt is mono-ammonium phosphate.

12. The method of claim 11 in which the mono-ammonium phosphate is administered to the patient in an amount from about 1 gram to about 3 grams every half hour.

* * * * *